(12) United States Patent
Schaefer et al.

(10) Patent No.: US 6,900,350 B2
(45) Date of Patent: May 31, 2005

(54) METHOD FOR THE PRODUCTION OF ω-AMINOALKYLSULPHONIC ACIDS

(75) Inventors: Volker Schaefer, Altrip (DE); Wolfgang Knoll, Weisenheim (DE); Alexander Schmitt, Roedersheim-Gronau (DE); Christoph Huettner, Weinheim-Luetzelsachsen (DE)

(73) Assignee: RASCHIG GmbH, Ludwigshafen (DE)

( * ) Notice: Subject to any disclaimer, the term of this patent is extended or adjusted under 35 U.S.C. 154(b) by 0 days.

(21) Appl. No.: 10/275,753

(22) PCT Filed: Apr. 27, 2001

(86) PCT No.: PCT/EP01/04754

§ 371 (c)(1),
(2), (4) Date: Nov. 8, 2002

(87) PCT Pub. No.: WO01/85678

PCT Pub. Date: Nov. 15, 2001

(65) Prior Publication Data

US 2003/0187295 A1 Oct. 2, 2003

(30) Foreign Application Priority Data

May 10, 2000 (DE) .......................................... 100 21 790

(51) Int. Cl.[7] .................... C07C 309/14; C07D 295/088
(52) U.S. Cl. ...................... 562/104; 544/59; 544/158; 544/398; 546/248; 548/574; 562/30
(58) Field of Search ..................... 562/30, 104; 544/59, 544/158, 398; 546/248; 548/574

(56) References Cited

U.S. PATENT DOCUMENTS

| | | | | |
|---|---|---|---|---|
| 1,932,907 A | * | 10/1933 | Nicodemus et al. | 562/104 |
| 4,238,609 A | * | 12/1980 | Mizuguchi et al. | 544/158 |
| 4,381,980 A | * | 5/1983 | Ballschuh et al. | 204/157.64 |
| 4,657,704 A | | 4/1987 | Yamamoto et al. | |
| 4,939,291 A | * | 7/1990 | Reiner | 562/108 |

FOREIGN PATENT DOCUMENTS

| | | |
|---|---|---|
| DE | 33 90 188 C2 | 7/1987 |
| EP | 0 752 420 A1 | 1/1997 |
| JP | 8-157444 A | 6/1996 |

OTHER PUBLICATIONS

Analytical Chemistry 71 pp. 333–334 by Jiang et al 1999.*
CA:99:37752 abs of JACS by Doi et al 105(14) pp 4684 1983.*
CA:127:308616 abs of Industrial & Engineering Chemistry Research 36(12) pp 5399–5402 1997.*
Patent Abstracts of Japan, C–274 Apr. 6, 1985, vol. 9, No. 78, JP 58–212465.
Patent Abstracts of Japan, vol. 1998, No. 09, Jul 31, 1998, JP 10 087601.
J.F. King et al., "The mechanism of hydrolysis of 2–hydroxyethanesulphonyl chloride: the intermediacy of 1,2–oxathietane 2,2–dioxide (beta–sultone)", Canadian Journal of Chemistry, vol. 67, No. 12, Dec. 1989, pp. 2162–2172.
Chemical Abstracts, vol. 92, No. 13, Mar. 31, 1980, Abstract No. 110477T, A. Zicmanis, et al, "3–Aminopropanesulphonic acids", p. 614.
W. Schliemann, et al., "Untersuchungen zur Synthese einiger 1-(p-Fluorphenyl)-1-pyrid-2'-ylbutylamine", Die Pharmazie, vol. 35, No. 2, Feb. 1980, pp. 69–72.

* cited by examiner

*Primary Examiner*—Peter G. O'Sullivan
(74) *Attorney, Agent, or Firm*—Foley & Lardner LLP

(57) ABSTRACT

The invention relates to a method for the production of ω-aminoalkylsulphonic acids of general formula (I), where R1 and R2=optionally substituted alkyl groups with 1 20 C atoms and n=a whole number from 2 6, whereby an amine of formula (II), where R1 and R2 have the above meanings is reacted with an alkyl dihalide of formula (III), where n has the above meaning and $X_1$ and $X_2$=chlorine or bromine, with addition of alkali hydroxide at a pH of 8 10. The pH is then adjusted to a value of 0 1, by addition of a hydrohalic acid and excess alkyl dihalide is separated off, before the reaction solution is adjusted to a pH of 6 7.5 with alkali liquor, alkali sulphite is added and the product (I) formed at elevated temperate.

9 Claims, 1 Drawing Sheet

METHOD FOR THE PRODUCTION OF ω-AMINOALKYLSULPHONIC ACIDS

BACKGROUND OF THE INVENTION

The present invention concerns a new process for the preparation of ω-aminoalkane-sulphonic acids in aqueous solution.

STATE OF THE ART

Aminoalkane-sulphonic acids belong to the group of the sulphonamides of the general formula I

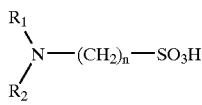

I whereby $R_1$ and $R_2$ are alkyl groups and n a whole number from 1 to 5.

The preparation of a group in these compounds with n=3 takes place, according to the prior art, according to the general reaction equation:

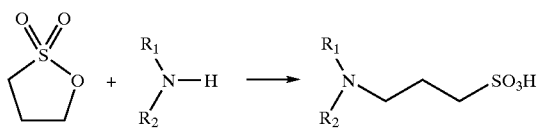

The 1,3-propanesultone used for this process hereby reacts as highly reactive agent also with weak nucleophiles. However, in the high reactivity is also based a high physiological potential.

Therefore, the alkane sultones are also classified as potentially cancer-producing and, for this reason, the use is disadvantageous. However, in general, the yield of this reaction generally lies at 95 to 98 percent so that hitherto it represents the technically most important manner of preparation.

Examples for technically used alkane-sulphonic acids are: 2-morpholino-ethane-sulphonic acid and 4-(2-hydroxyethyl)-1-piperazine-propane-sulphonic acid. These compounds serve, inter alia, as biological buffer substances in cell cultures.

EP 0 752 420 A1 describes a process for the preparation of 3-pyridinium-propane sulphone betaine (PPS) with avoidance of 1,3-propane-sultone, whereby pyridine is reacted with 1,3-dihalopropane and sodium sulphite in the presence of water and an alkyl halide as solvent.

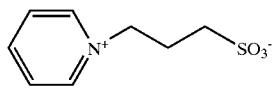

However, the process is only suitable for tertiary amine components which carry no hydrogen on the amine nitrogen. In the case of the use of secondary amines, there namely takes place a deprotonisation of the tertiary ammonium salt formed by still not reacted secondary amine since the the secondary amine represents a stronger base than a tertiary amine and the resulting quaternary nitrogen carries an easily split off hydrogen. Liberated tertiary amine can thereby again react with the dihalopropane and therewith form undesired quaternary products in the sense of the following equation:

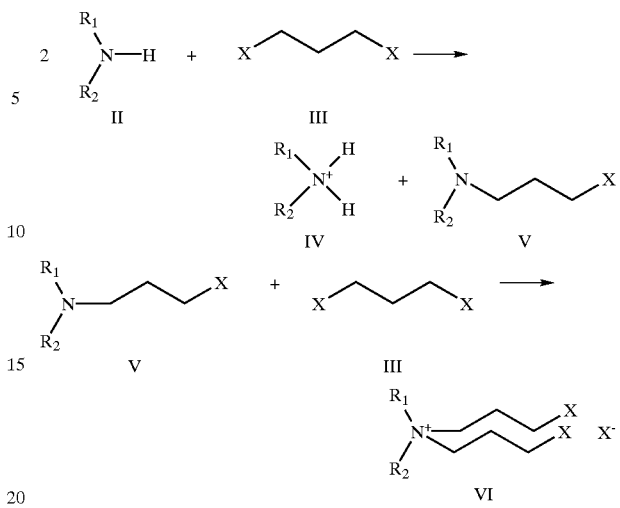

Besides the desired intermediate compound V, this leads to the no longer further reacting ammonium halide salt IV and the undesired quaternary salt VI. This leads to considerable yield reductions and high proportions of by-products.

Furthermore, there is given a high burdening of the solutions obtained with alkali halides. However, in the case of the required high purity of the end products, for example as biobuffer, this is not acceptable so that, according to the known preparation process, an isolation and purification of the solid aminoalkane-sulphonic acids must take place.

Thus, hitherto no access is open to sulphoalkylated, for example sulphopropylated, secondary amine compounds with exclusion of alkanesultones.

SUMMARY OF THE INVENTION

Therefore, the task exists to find a process with which also ω-aminoalkane-sulphonic acids can be prepared economically without alkanesultones and which preferably also permits a purification of the solutions obtained without isolation of the solid products.

Consequently, the invention concerns a process for the preparation of aminoalkane-sulphonic acids, preferably as aqueous solution, without use of alkanesultones. Furthermore, the purification of the solutions obtained and the steps necessary for the obtaining of the pure substances. It is also a further object of the new process to obtain high yields as in the case of the alkanesultone process with equal product quality. Therefore, possible side reactions must be suppressed, as well as a possibly complete reaction of the materials used being achieved.

DETAILED DESCRIPTION OF PREFERRED EMBODIMENTS

Figure 1:
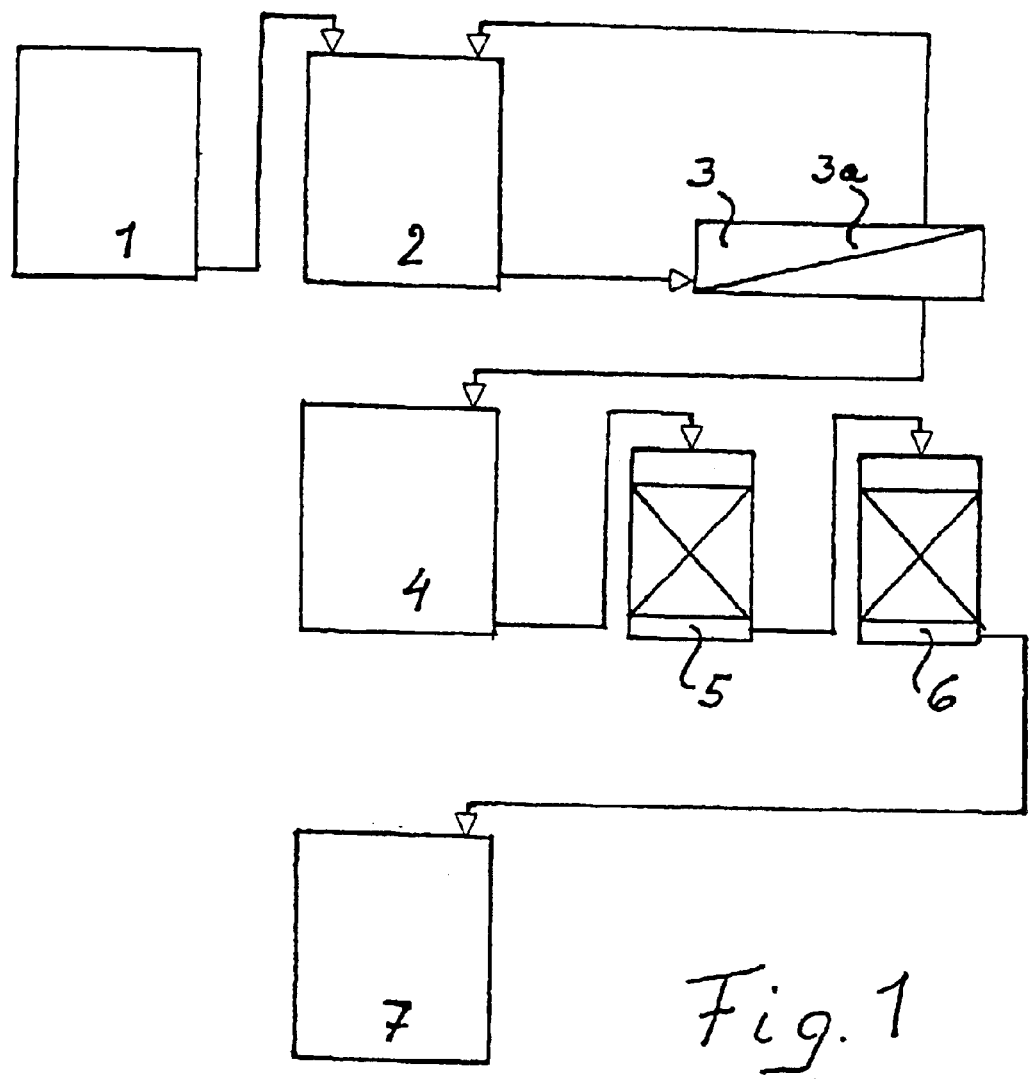
FIG. 1 is a schematic representation of the nanofiltration and ion exchange process steps.

Since it is not possible to bring secondary amines directly to reaction with dihaloalkanes and alkali metal sulphite free of by-products, it is necessary to use a new process for the preparation.

One hereby starts from secondary amines which are brought to reaction with dihaloalkanes is such a manner that the addition of alkaline lye takes place. This is necessary in order to suppress possible side reactions. One works in water-containing media.

In a second step, the addition of hydrohalic acid to the reaction solution is necessary in order to achieve an acid pH range favourable for the further steps of the preparation process.

For the formation of the sulphonic acid, alkali metal sulphite is added to the reaction solution in amounts equimolar to the amine.

The amounts contained of alkali metal halides, as well as the by-products resulting in traces, act disturbingly for the direct use of the products obtained, for example of the buffer substance. In order to obtain the product in the purity required for the biobuffer solution, after the reaction a purification of the aqueous reaction medium must be carried out. It is hereby to be taken into account that per 1 mol of the reaction product at least 2 mol of alkali metal halide result. On the basis of a small excess of alkali metal sulphite in the reaction batch, the proportion of alkali metal salts in the product solution is, however, also additionally increased by this amount. A depletion of the alkali metal halides and by-products can now, for example, be carried out by means of ion exchange processes. However, because of the high content of alkali metal halides formed, this cannot be carried out economically. The nanofiltration process alone does not suffice for technical reasons to achieve the required product purity since in the nanofiltration all negative divalent charged particles and larger molecules, such as result as by-products are also held back and thus remain in the product solution.

The product purification described in the present invention now refers to the combination of nanofiltration and ion exchange process for the economic separation of of the product from the mono- and divalent alkali halides and by-products resulting during the reaction. The process of nanofiltration used in the scope of this invention and the ion exchange by means of ion exchange resins are known.

The nanofiltration hereby serves for the depletion of the monovalent alkyl halides. The divalent alkali halides and remaining by-products, which account for a combined proportion of about 0.5 wt. %, are removed in a second step by means of ion exchange processes. The carrying out of the process according to the invention is described in the following in general form.

The Nanofiltration

The osmotic pressure of the reaction solution, which must be overcome during the nanofiltration for the depletion of the monovalent alkali halides, is determined by the concentration of the product, of the by-products and of the divalent alkali salts. In the usual reaction solution, this osmotic pressure amounts to about 30 bar. For the carrying out of the nanofiltration at technically and economically meaningful operating pressures, the reaction solution must, therefore, be diluted with water in a ratio of 1:2 to 1:3, whereby the osmotic pressure is reduced in the same way to 15–10 bar. The nanofiltration process is preferably carried out in the process manner of the diafiltration. For a sufficient depletion of the alkali halides, demineralised water is used as diafiltration solution. The diafiltrate volume corresponds to about 7 to 10 fold or the reaction solution. A depletion of the monovalent alkali halides to >95% is therewith possible. There is used a nanofiltration membrane with a cut-off of about 150–300 g/mol, preferably about 200 g/mol and an operating pressure of 25–35 bar, i.e. 15–20 bar higher than the osmotic pressure. Subsequently to the diafiltration, partly purified reaction solution is now concentrated to the original volume and further purified by ion exchange processes.

Ion Exchange Process

The exchange of anions and cations by means of ion exchange resins has long since been used and is prior art. The here-described purification is carried out with a combination of strongly acidic cation exchange and weakly basic anion exchange. There was used, for example, a strongly acidic ion exchanger of a type Pyrolite C 104 and, as weakly basic ion exchanger a type Pyrolite A 100. The manner of operation of the ion exchanger is to be carried out in a co-current or countercurrent process, the co-current principle is preferred. The ratio of anionic and cationic exchanger is so adjusted that the following anionic exchanger has the same exchanger capacity as the cationic exchanger. The capacity of the ion exchanger suffices in order to deplete a reaction volume pre-purified by the nanofiltration corresponding to the 8–10 fold bed volume of the cation exchanger. The ion exchange process makes possible a depletion of the alkali halides and by-products to less than 0.1%. For the elution of the product remaining in the ion exchanger, the ion exchanger columns are washed out with demineralised water. The wash water volume corresponds to about 2–3 fold bed volume, of the cation exchanger. The regeneration of the ion exchanger takes place according to the technical instructions of the manufacturer.

In the accompanying FIG. 1 is given the flow diagram of the combination according to the invention of nanofiltration and ion exchange for the product purification. In this Figure, the diafiltrate is passed over from the container 1 into the product container 2 from which it runs into the nanofiltration 3 in which the nanofiltration membrane 3a is indicated by the diagonal line. The proportions not passing the membrane are returned into the product solution and there diluted back with diafiltrate to the purification concentration. The purified solution running through the membrane 3a passes via an intermediate tank 4 to the first ion exchanger column with a strongly cationic exchanger 5 and its run-off to a second ion exchanger column with weakly anionic exchanger 6. The product purified by these ion exchangers is collected in the collection tank 7 and removed as required.

PROCESS EXAMPLE

Preparation of 3-morpholinopropane-sulphonic acid Solution ω-(MOPS)

6298 g (40 mol) of 1,3-bromo-chloropropane (BCP) was taken and warmed to 20° C., 420 g (10 mol) NaOH in 2000 ml water was added thereto and subsequently 870 g (10 mol) morpholine added thereto.

After 10 min, the suspension was heated to 45° C. It as stirred at this temperature for 8 hours.

100 ml 33% hydrochloric acid in 1250 g water was added thereto in slight excess (about 11 mol). The amount of hydrochloric acid is thereby not to be observed but rather the pH value. First when this has sunk to 0 to 1, a sharp separation between aqueous and organic phase took place.

The organic phase (excess BCP) was run off.

To the aqueous phase is added concentrated soda lye up to a pH value of 5–6 and subsequently a saturated sodium sulphite solution (1260 g (10 mol) NaSO$_3$+ 1250 g H$_2$O) added thereto.

The mixture was heated to 75° C. and stirred at this temperature for 24 hours.

Thereafter, the solution was cooled and purified as follows.

Purification by Means of Nanofiltration and Ion Exchange

There were used 7.8 kg (6.5 liter) of the salt-containing product solution from the preparation of ω-MOPS. The product solution contained 1.21 kg ω-MOPS, 0.73 kg NaCl, 0.6 kg NaBr and 0.04 kg $Na_2SO_4$. The separation of the monovalent salts NaCl and NaBr was carried out by means of nanofiltration. For the reduction of the osmotic pressure of the solution, the product solution was diluted with 6.5 liters demineralised water. The nanofiltration was carried out in the form of a diafiltration with a conventional spool module. There was used a spool module of the firm Osmonic with a cut-off of 250 Dalton and a membrane surface of 1 $m^2$. The nanofiltration took place in the case of a transmembrane pressure of 35 bar and a flowing over of the membrane of 1000 $l/m^2h$.

The nanofiltration was carried out as follows: The salt-containing product solution was placed in the storage container of the nanofiltration plant and diluted with 6.5 liters of demineralised water. The permeate volume running off (average permeate flow 50 l/h) was continuously replaced in the storage container by demineralised water in the same ratio. (diafiltration). The nanofiltration was carried out until a permeate volume of 100 liters was removed from the system. Thereafter, a concentration of the now substantially desalinated product solution was carried out until the original volume of 6.5 liters was again reached. After the diafiltration of the reaction medium, a concentration of 100 liters of permeate to an end volume of 7.5 liters was carried out. The adjustment was here a membrane flowing over of 1000 $l/m^2h$ and a transmembrane pressure of 30 bar, The concentrated permeate and the partly desalinated product solution were thereafter mixed with one another (in the following called prepurified product solution), The permeate concentration had the purpose again to recover about 90% of the MOPS from the permeate and thus to increase the product-referred total recovery in the nanofiltration from 90% to over 99%.

After the nanofiltration, the mixture of partly desalinated product solution and concentrated permeate contained 1.20 kg ω-MOPS, 0.045 kg NaCl, 0.037 kg NaBr and 0.04 kg $Na_2SO_4$. Thus, the nanofiltration makes possible a reduction of NaCl by 94% and of NaBr of 95% in the case of a product loss smaller than 1%, the content of sodium sulphate is not reduced.

Subsequent to the nanofiltration, there took place the separating off of the sodium sulphate and of the remaining salts from the pre-purified solution by means of ion exchange processes. One liter of pre-purified product solution contained 0.144 kg ω-MOPS, 2.8 g NaCl, 3.5 g NaBr and 3 g $Na_2SO_4$. There was here used an arrangement of two columns with 350 ml of strongly cationic ion exchanger Relite EXC08 and 170 ml of the weakly anionic exchanger Relite EXA54. The loading capacity of the ion exchange material suffices in order completely to desalinate 1 liter of pre-purified product solution. The ion exchangers are used in their correspondingly regenerated form (H-form for strongly cationic and OH-form for weakly anionic). The pre-purified product solution was first passed over the strongly cationic ion exchanger and thereafter over the weakly anionic ion exchanger. The flow throught of the pre-purified product solution through the ion exchangers took place by the hydrostatic pressure. Thereafter, both ion exchangers were rinsed with 1 liter of demineralised water. The rinse water and the now completely purified product solution are mixed with one another and this mixture gave 2 liters of product solution. After the purification by means of ion exchange processes, the product solution contained 0.138 kg ω-MOPS and no more detectable salts. This corresponded to a product loss smaller than 4%. The purification was herewith ended.

What is claimed is:

1. A process for the preparation of an ω-aminoalkyl-sulphonic acid from a secondary amine, an alkyl dihalide, and an alkali metal sulphite, comprising the steps of:
   (a) reacting a secondary amine with an alkyl dihalide in an aqueous solution at a pH value of 8–10, wherein the pH is maintained by the addition of an alkali metal hydroxide, to produce an intermediate solution;
   (b) adjusting the intermediate solution to a pH value of 0–1 by the addition of a hydrohalic acid;
   (c) after step (b), separating off excess alkyl dihalide;
   (d) after step (c), adjusting the pH value of the intermediate solution to 6–7.5 by addition of an alkali metal hydroxide;
   (e) after step (d), adding an alkali metal sulphite; and
   (f) conducting a reaction at elevated temperature to form a solution containing ω-aminoalkyl-sulphonic acid.

2. The process according to claim 1, wherein the secondary amine is of the formula II:

II in which $R_1$ and $R_2$ are the same or different and represent a straight-chained or branched alkyl groups with 1–20 C-atoms or, together with the nitrogen atom, form a 5- or 6-membered saturated aliphatic ring, wherein 1 or 2 members of the ring can thereby also be N—$R_3$, O or S instead of $CH_2$, and $R_3$ represents hydrogen or an alkyl group with 1–20 C-atoms.

3. The process according to claim 1, wherein the alkyl dihalide has the formula III:

III in which n represents a whole number of 1–5, and $X_1$ and $X_2$ are chlorine or bromine atoms.

4. The process according to claim 3, wherein. $X_1$ and $X_2$ are chlorine atoms.

5. The process according to claim 1, wherein the alkali metal in each instance is sodium.

6. The process according to claim 1, wherein the alkyl dihalide is an alkyl dichloride.

7. The process according to claim 1, further comprising step:
   (g) subjecting the ω-aminoalkyl-sulphonic acid solution to nanofiltration to separate it from alkali metal halides and alkali metal sulphites contained therein.

8. The process according to claim 7, wherein, prior to nanofiltration, the solution is adjusted to a concentration whereat the osmotic pressure for nanofiltration is 10–20 bar.

9. The process according to claim 7, further comprising step:
   (h) after the nanofiltration, purifying the solution by means of ion exchange chromatography with a strongly acidic cation exchanger and a weakly basic anion exchanger, to produce an ω-aminoalkyl-sulphonic acid solution essentially free of remaining salts, nonampho-teric starting materials, and nonamphoteric by-products.

* * * * *